United States Patent
Kalin et al.

(10) Patent No.: US 6,427,541 B1
(45) Date of Patent: Aug. 6, 2002

(54) APPARATUS FOR TESTING ROLLING CONTACT FATIGUE RESISTANCE OF MATERIALS WITH POSSIBLE INTERRUPTIONS

(76) Inventors: Mitjan Kalin, Cankarjeva 24, 5000 Nova Gorica; Joze Vizintin, Azmanova 34, 1000 Ljubljana, both of (SI)

( * ) Notice: Subject to any disclaimer, the term of this patent is extended or adjusted under 35 U.S.C. 154(b) by 0 days.

(21) Appl. No.: 09/455,638

(22) Filed: Dec. 7, 1999

(30) Foreign Application Priority Data

Jan. 15, 1999 (SI) ................................................ 9900005

(51) Int. Cl.⁷ ................................................ G01N 3/08
(52) U.S. Cl. ...................................................... 73/829
(58) Field of Search .......................... 73/829, 7, 866.4, 73/118.1; 148/584

(56) References Cited

U.S. PATENT DOCUMENTS 4,452,065 A * 6/1984 Minter ............................ 73/7
5,837,882 A * 11/1998 Bacigalupo et al. .......... 73/781

* cited by examiner

Primary Examiner—Benjamin R. Fuller
Assistant Examiner—Octavia Davis
(74) Attorney, Agent, or Firm—Jackson Walker LLP

(57) ABSTRACT

The present invention is an apparatus for testing the rolling contact fatigue resistance of materials that enables the interruption of testing as well as the continuation of testing from a defined prior state. During testing of the rolling contact fatigue resistance of materials along a surface of the tested object, a testing ball is rolled under appropriate loading and numerous repetitions. The present invention ensures that the appropriate point contact is maintained between the testing ball and the surface of the tested object. The tested object is firmly held in by a clamping plate having a series of supporting protrusions separately arranged in grooves. The position of each protrusion may be fixed within its respective groove to provide a stable mounting area for the tested object. The present invention allows the tested object to be removed and replaced such that a test performed upon the tested object prior to its removal from the clamping unit may be continued upon reinsertion of the tested object.

3 Claims, 2 Drawing Sheets

APPARATUS FOR TESTING ROLLING CONTACT FATIGUE RESISTANCE OF MATERIALS WITH POSSIBLE INTERRUPTIONS

The present invention relates to an apparatus for testing rolling contact fatigue resistance of materials with possible interruptions. During rolling contact fatigue resistance of materials testing, an appropriate testing ball is rolled under certain loading and numerous repetitions along the surface of a tested object, while between the ball and the surface of the tested object a point contact is ensured.

It is the aim of the invention to conceive a simple and useful apparatus for testing the rolling contact fatigue resistance of various materials. The present invention enables the interruptions of testing as well as the continuation of testing from a defined prior state.

It is known (e.g., from technical descriptions of available testing systems manufactured by FAG Kugelfischer Georg Schaefer A G) that devices for testing rolling contact fatigue resistance of materials mainly consist of a clamping unit, a loading unit and a driving assembly. The loading unit enables clamping of a testing ball of a predetermined diameter into a clamping area in which the ball can rotate freely and be turned in all directions. The loading unit can be turned so that the clamping area is rotatable around an axis, by which moving the testing ball along a circular path of a pre-defined diameter is enabled. Furthermore, the loading unit ensures the appropriate loading of the testing ball such that the ball is pressed against the corresponding tested object. A driving assembly consists of appropriate driving and bearing parts, which enable turning of the testing ball under loading along the surface of the tested object.

The clamping unit of such a device is arranged to enable firm clamping of a tested object, bearing in mind the loading of the testing ball as well as the movement of the ball along a circular path during testing. The clamping unit has clamps used to prevent movement of the tested object from the clamping unit due to the loading and circular rolling movement of the ball along the surface of the tested object.

Although relatively complicated, such a device enables satisfactory clamping of the tested object during ordinary testing of rolling contact fatigue resistance of materials. However, it is desirable to observe the tested object after subjection to testing. For example, the tested object may be observed after a certain time period has elapsed or after a number of repetitions under loading have occurred in order to make conclusions. Using known devices, the test must be interrupted in order to enable observations and measurements. Another test must then be performed for observation and measurement of the state of the tested object occurring in the next stage.

When using known devices, observation of the state of the tested object after certain stages during testing is possible only by means of several identical tested objects being separately exposed to the same testing up to different stages. In such a manner, the first tested object has to be clamped and thereafter exposed to rolling contact loading for a certain time and for a certain number of repetitions under loading. The tested object must be removed from the clamping unit so that it may be observed and measured. The testing must be repeated using another tested object (e.g., exposed to the same loading for a longer time period), so that more repetitions of loading can be achieved. This approach requires a large number of tested objects to be used and tested, thus resulting in additional time and expense.

Accordingly, an apparatus for testing rolling contact fatigue resistance of materials capable of continued testing after an interruption is provided. The present invention has a driving assembly connected and driven by a loading unit having a testing ball for rolling along the testing surface of each tested object as clamped in the clamping unit. The loading unit has a guide plate, by which at least one rolling position end of the testing ball is unique and repeatably defined, a clamping unit having a clamping area for receiving a tested object, and grooves arranged adjacent thereto for receiving protrusions. The protrusions being smoothly movable along the grooves and attachable in their appropriate positions to prevent movement along each protrusion's respective groove. In one embodiment of the invention, the guide plate is attached on the bottom side of the loading unit in the direction of the tested object, while the testing ball is at least partially surrounded by a guide plate in the area of its equatorial plane being parallel to the testing surface of the tested object. The guide plate is designed to enable the rolling movement of the testing ball along the tested object in the plane lying parallel to the testing plane in the longitudinal direction such that simultaneous rolling movement of the testing ball in the transversal direction in the same plane is permitted.

Each groove of the clamping plate is equipped with a threaded bore in its bottom. Each protrusion is equipped with a slotted opening extending in the longitudinal direction of its respective groove. Each protrusion is capable of being fixed in an appropriate position within its respective groove while being rested against the tested object by means of a screw. Each screw being inserted through each protrusion's respective slotted bore and screwed into the belonging screw bore located at the bottom of the protrusion's respective groove. The clamping plate has at least one slotted bore to facilitate attachment of the plate to an appropriate support.

An apparatus will be now described in more detail on the basis of an embodiment as disclosed in the accompanied drawings, wherein, FIG. 1 is a front view of an apparatus for testing rolling contact fatigue resistance of materials;

Figure 1:
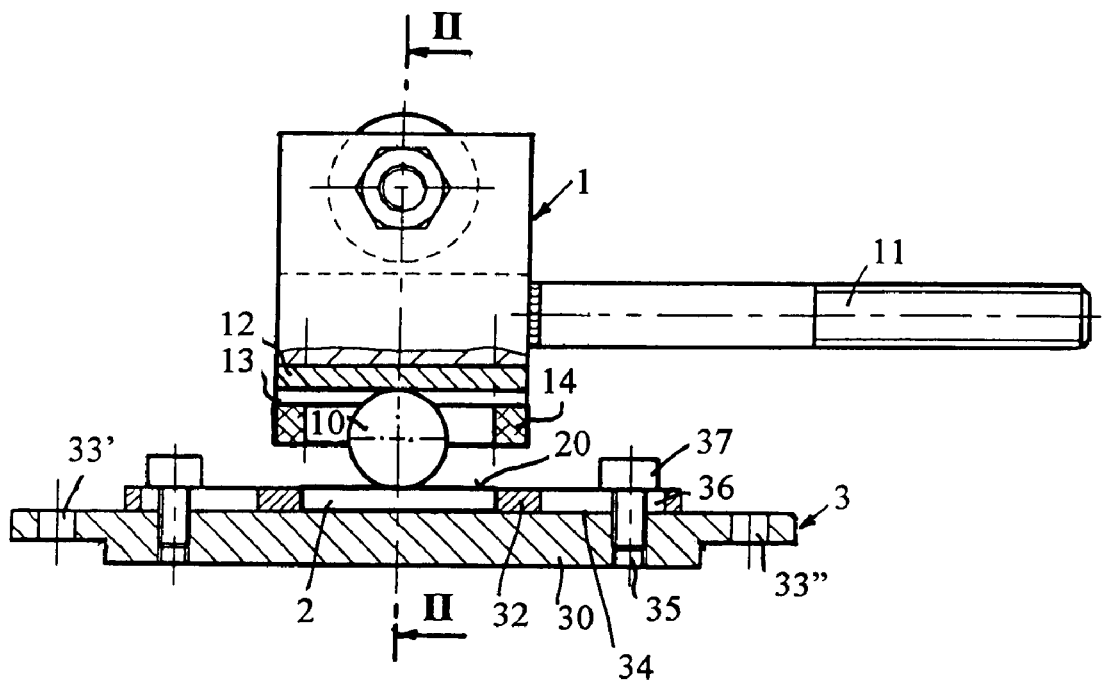
Figure 2:
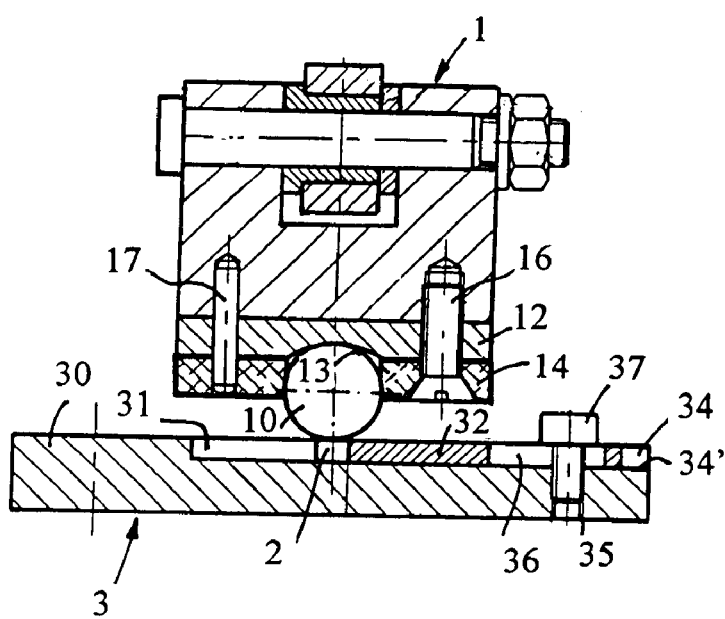
FIG. 2 is a cross-section along the plan II—II according to FIG. 1.
Figure 3:
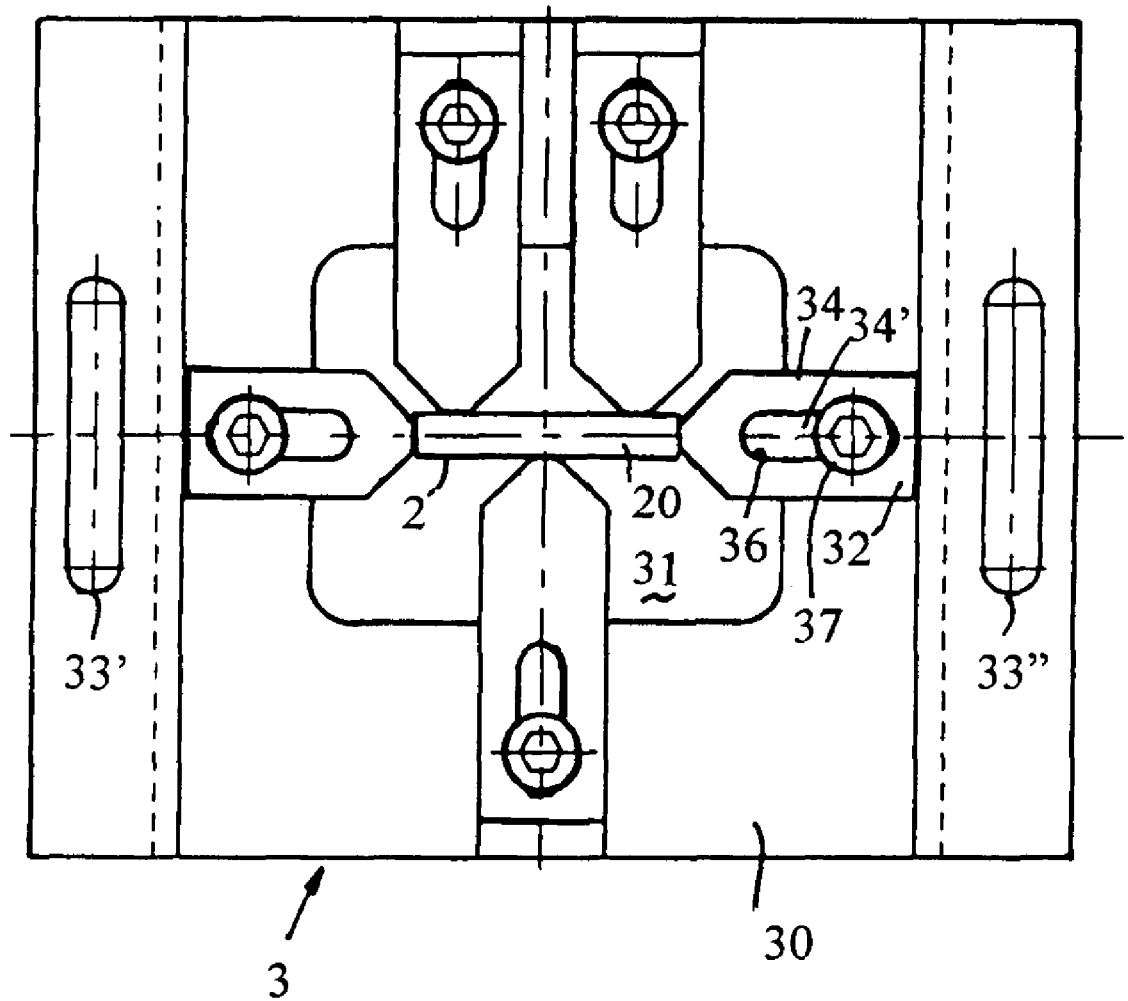
FIG. 3 is a plan view of a clamping unit of an apparatus according to the invention.

One embodiment of the invention as shown in FIGS. 1–3 enables an improved manner of testing the rolling contact fatigue resistance using an improved testing apparatus. The present invention comprises a testing ball (10) capable of linear oscillatory rolling along a surface (20) of the tested object (2). A loading unit (1), a driving assembly (not shown) and a clamping unit (3) capable of holding tested object (2) is provided. Different shapes and embodiments of the tested object (2) may be chosen, but in each case the tested object (2) has at least one flat surface (20) having a length as required for performing each test.

In one embodiment, the loading unit (1) has a threaded shaft (11) connected to the driving assembly (not shown). The threaded shaft (11) of the loading unit (1) may be any appropriate crank drive known to those skilled in the art. The bottom side of the loading unit (1), in the direction of tested object (2) has a bearing surface (12) comprising a recess (13) extending in the longitudinal direction with respect to the surface (20) of the tested object (2) such that the testing ball (1) may be supported. A guide plate (14) is attached to the bearing surface (12) using pins (17) and screws (16). The testing ball (10) is partially surrounded in its equatorial plane respectively in its diametrical plane lying parallel to the surface (20) of the tested object (2) by the guide plate (14) such that only limited rolling movement of the testing ball (10) along the surface (20) of the tested object (2) is allowed. Specifically, movement in the longitudinal direction with respect to the recess (13) is allowed, thus excluding any movement in the transversal direction with respect to the recess (13).

The clamping unit (3) has a clamping plate (30) equipped with a clamping area (31) and moreover with several—by the shown embodiment there are five—supporting protrusions (32) separately arranged in appropriate grooves (34). The clamping plate (30) is attached to appropriate support using screws (not shown); two slotted holes (33' and 33", respectively) are provided for this purpose.

The clamping plate (30) has several grooves (34) arranged adjacently to the clamping area (31). At least one threaded bore (35) is provided in the bottom (34') of each groove (34). The protrusions (32) are placed within the grooves (34) such that each protrusion may be slightly moved along the groove (34) to which it is affixed. Each protrusion (32) is equipped with a slotted bore (36) extending in the longitudinal direction with respect to the groove (34). This allows each protrusion (32) to be fixed along its respective groove (34) in the desired position. Each protrusion is held in place using a screw (37) inserted through the slotted bore (36) of its respective groove (34) and screwed into the threaded bore (35) in the bottom (34) of the groove (34) of the clamping plate (30).

During preparation for testing, the tested object (2) is positioned and directed such that a sufficient testing surface (20), as required, for successful testing is available. The tested object is placed in the clamping area (31) of the clamping plate (30) and clamped in the clamping unit (3). Loose screws (37) enable each protrusion (32) to slide along its respective groove (34) such that each protrusion (32) may be pressed against the tested object (2) and fixed thereafter in position by tightening the respective screw (37). In such a manner, the tested object (2) may be clamped within the clamping unit (3) for testing. Due to the unique design of the guide plate (14), the testing ball (10), as placed with the recess (13) of the bearing surface (12) may be moved to;one of both available end positions with respect to the recess (13) of the bearing surface (12). This allows testing to be initiated such that the appropriately loaded testing ball (10) may be rolled along the testing surface (20) of the tested object (2). The present invention allows rolling contact failure testing to be interrupted and resumed upon the same tested object.

To accomplish this, the loading unit (1) is moved such that the testing ball (10) rests in one of the end positions as defined by the guide plate (14). Alternatively, the tested object (2) may be released from the clamping area (31) by disengaging the belonging screws (37) of as few as two of five protrusions (32). For example, only the left and the bottom (e.g., the right and bottom screw (37)) are released, and the remaining three protrusions (32) remain in their fixed position. This allows the tested object (2) to be temporarily removed from the clamping area. (31) and returned to the same position by adjusting only two protrusions (32).

Whenever the testing operation is interrupted, the measures taken in the course of positioning the testing ball (10) and the tested object (2) allows the tested object (2) to be removed from the clamping unit (3) and then (e.g., after measuring or observing wherever performed) returned to their original (2) position for continued testing. The present invention allows the tested object (2) to be repeatedly measured and observed at various stages of the testing process without the loss of testing accuracy.

What is claimed is:

1. An apparatus for testing rolling contact fatigue with possible interruptions comprising a loading unit having a testing ball for rolling along a testing surface of a tested object, said loading unit having a guide plate defining a rolling position of said testing ball, said guide plate being attached to a bottom side of said loading unit in the direction of said tested object such that said guide plate extends parallel to said testing surface of said tested object such that said testing ball is partially surrounded by said guide plate at said testing ball's equatorial plane;

a driving assembly connected to said loading unit, said driving assembly capable of driving said loading unit;

a clamping unit having a clamping area for receiving said tested object and grooves adjacent thereto for receiving five protrusions being adjustably secured to each of said grooves, each of said protrusions having a slotted bore extending in a longitudinal direction with regard to each of said grooves, each of said protrusions capable of releasably securing said tested object; and said protrusions being arranged upon said clamping unit to allow the removal of said tested object from said clamping unit upon adjustment of only two of said five protrusions, the remaining three of said five protrusions being held firmly in place to provide positional guidance for said tested object such that said tested object may be reinserted for subsequent testing at substantially the same location occupied by said tested object prior to the removal of said tested object from said clamping unit.

2. The apparatus of claim 1, wherein each of said protrusions may be releaseably secured to each said groove by inserting a screw through said slotted bore of said protrusions such that said screw releaseably attaches to said threaded bore.

3. The apparatus according to any one of the proceeding claims, wherein said clamping unit comprises at least one slotted bore for attaching said clamping unit to an appropriate support.

* * * * *